US010980963B1

(12) United States Patent
Groll et al.

(10) Patent No.: US 10,980,963 B1
(45) Date of Patent: *Apr. 20, 2021

(54) CLOTH RESPIRATORY MASK

(71) Applicant: Circadiance, LLC, Turtle Creek, PA (US)

(72) Inventors: David Groll, Murrysville, PA (US); Ronnie E. Mahofski, North Huntingdon, PA (US); Nadine Scandinaro, Export, PA (US); Eric S. Nachreiner, Glenshaw, PA (US)

(73) Assignee: Circadiance LLC, Turtle Creek, PA (US)

( * ) Notice: Subject to any disclaimer, the term of this patent is extended or adjusted under 35 U.S.C. 154(b) by 440 days.

This patent is subject to a terminal disclaimer.

(21) Appl. No.: 15/962,259

(22) Filed: Apr. 25, 2018

Related U.S. Application Data

(63) Continuation of application No. 13/844,706, filed on Mar. 15, 2013, now Pat. No. 9,981,104, which is a continuation-in-part of application No. 13/831,239, filed on Mar. 14, 2013, now Pat. No. 9,308,343, and a continuation-in-part of application No. 12/905,404, filed on Oct. 15, 2010, now abandoned, and a continuation-in-part of application No. 12/070,463, filed on Feb. 19, 2008, now abandoned.

(51) Int. Cl.
*A61M 16/06* (2006.01)
*A61M 16/00* (2006.01)
*A61M 16/08* (2006.01)

(52) U.S. Cl.
CPC .... *A61M 16/0683* (2013.01); *A61M 16/0057* (2013.01); *A61M 16/0816* (2013.01)

(58) Field of Classification Search
CPC ........................................... A41D 13/11–1192
See application file for complete search history.

(56) References Cited

U.S. PATENT DOCUMENTS

| 2,435,721 A | 2/1948 | Lehmann |
| 2,641,253 A | 6/1953 | Engelder |
| 3,357,426 A | 12/1967 | Cohen |
| 3,750,665 A | 8/1973 | Stranicky |
| 3,802,428 A | 4/1974 | Sherman |
| 4,484,575 A | 11/1984 | Brockway |
| 4,890,609 A * | 1/1990 | Wilson, II ............. A61M 16/06 128/206.28 |
| 4,971,051 A | 11/1990 | Toffolon |
| 5,243,971 A | 9/1993 | Sullivan |
| 5,269,296 A | 12/1993 | Landis |
| 5,322,695 A | 6/1994 | Apostolopoulos |

(Continued)

FOREIGN PATENT DOCUMENTS

| AU | 2009215562 S2 | 2/2012 |
| FR | 2917296 A1 | 9/2006 |

(Continued)

*Primary Examiner* — Rachel T Sippel
(74) *Attorney, Agent, or Firm* — Metz Lewis Brodman Must O'Keefe LLC (57) ABSTRACT

A respiratory mask made of cloth and having a nasal portion and an air delivery arrangement is disclosed. The cloth that is used is impermeable to air and is designed to provide a mask that will inflate to provide therapy to patients at a positive pressure. The air delivery arrangement provides air at positive pressure to the body of the mask via a hermetic seal.

19 Claims, 8 Drawing Sheets

(56) References Cited

U.S. PATENT DOCUMENTS

| | | | |
|---|---|---|---|
| 5,429,126 | A | 7/1995 | Bracken |
| 5,431,158 | A | 7/1995 | Tirotta |
| 5,490,501 | A | 2/1996 | Crowley |
| 5,538,000 | A | 7/1996 | Rudolph |
| 5,728,451 | A | 3/1998 | Langley |
| 5,746,201 | A | 5/1998 | Kidd |
| 6,044,844 | A | 4/2000 | Kwok |
| 6,269,814 | B1 | 8/2001 | Blaszczykiewicz |
| 6,338,340 | B1 | 1/2002 | Finch |
| 6,341,606 | B1 | 1/2002 | Bordewick |
| 6,357,440 | B1 | 3/2002 | Hansen |
| 6,510,818 | B2 | 1/2003 | Barney |
| 6,513,526 | B2 | 2/2003 | Kwok |
| 6,526,978 | B2 | 3/2003 | Dominguez |
| 6,634,358 | B2 | 10/2003 | Kwok |
| 6,698,427 | B1 | 3/2004 | Clowers |
| 6,701,927 | B2 | 3/2004 | Kwok |
| 6,749,923 | B1 | 6/2004 | Palumbo |
| 6,763,835 | B1 | 7/2004 | Grove |
| 6,871,649 | B2 | 3/2005 | Kwok |
| 6,938,620 | B2 | 9/2005 | Payne, Jr. |
| 7,036,508 | B2 | 5/2006 | Kwok |
| 7,127,278 | B2 | 10/2006 | Melker |
| 7,159,567 | B2 | 1/2007 | Drew |
| 7,178,525 | B2 | 2/2007 | Matula, Jr. |
| 7,188,620 | B2 | 3/2007 | Amarasinghe |
| 7,225,811 | B2 | 6/2007 | Ruiz |
| 7,347,229 | B2 | 3/2008 | Glenn |
| 7,406,966 | B2 | 8/2008 | Wondka |
| 7,481,220 | B2 | 1/2009 | Meyer |
| 7,481,221 | B2 | 1/2009 | Kuilik |
| 7,779,832 | B1 | 8/2010 | Ho |
| 2002/0162556 | A1 | 11/2002 | Smith |
| 2003/0004445 | A1 | 1/2003 | Hall |
| 2003/0131852 | A1 | 7/2003 | Shafer |
| 2003/0145857 | A1 | 8/2003 | Sullivan |
| 2005/0015860 | A1* | 1/2005 | Reaux .................... A61F 9/064 |
| | | | 2/424 |
| 2005/0061326 | A1 | 3/2005 | Payne, Jr. |
| 2005/0172968 | A1 | 8/2005 | Hishida |
| 2005/0199240 | A1 | 9/2005 | Hall |
| 2006/0027237 | A1 | 2/2006 | Sleeper |
| 2007/0131229 | A1 | 6/2007 | Madaus |
| 2007/0163595 | A1 | 7/2007 | Chen |
| 2007/0175479 | A1 | 8/2007 | Groll |
| 2007/0181135 | A1 | 8/2007 | Baker |
| 2007/0246043 | A1 | 10/2007 | Kwok |
| 2008/0047560 | A1 | 2/2008 | Veliss |
| 2008/0121235 | A1 | 5/2008 | Ging |
| 2008/0142015 | A1 | 6/2008 | Groll |
| 2008/0149104 | A1 | 6/2008 | Eifler |
| 2009/0032024 | A1* | 2/2009 | Burz .................. A61M 16/0605 |
| | | | 128/206.24 |
| 2009/0044808 | A1 | 2/2009 | Guney |
| 2009/0065005 | A1 | 3/2009 | Ades |
| 2009/0107504 | A1 | 4/2009 | McAuley |
| 2009/0211583 | A1 | 8/2009 | Carroll |
| 2009/0223518 | A1 | 9/2009 | Kwok |
| 2011/0146685 | A1 | 6/2011 | Allan |
| 2011/0209701 | A1 | 9/2011 | Derringer |
| 2011/0253144 | A1 | 10/2011 | Groll |
| 2012/0042878 | A1* | 2/2012 | Woo ..................... A41D 13/1138 |
| | | | 128/206.15 |
| 2012/0055485 | A1 | 3/2012 | Anthony |
| 2013/0074845 | A1 | 3/2013 | Smith |
| 2013/0152918 | A1 | 6/2013 | Rummery |
| 2013/0199537 | A1 | 8/2013 | Formica |
| 2014/0090649 | A1 | 4/2014 | Groll |
| 2014/0158136 | A1 | 8/2014 | Romagnoli |
| 2014/0299134 | A1 | 10/2014 | Matula |

FOREIGN PATENT DOCUMENTS

| | | |
|---|---|---|
| GB | 2470172 B2 | 8/2011 |
| WO | WO0050121 A1 | 2/2000 |
| WO | WO2004037153 A3 | 10/2003 |
| WO | WO2005028010 A3 | 9/2004 |
| WO | WO2007136376 A1 | 11/2007 |

* cited by examiner

CLOTH RESPIRATORY MASK

CROSS-REFERENCE TO RELATED APPLICATIONS

This patent application is a continuation of, and claims priority from, pending U.S. application Ser. No. 13/844,706, filed Mar. 15, 2013, which was a continuation-in-part of and claimed priority from pending U.S. application Ser. No. 12/070,463, filed Feb. 19, 2008, pending U.S. patent application Ser. No. 12/905,404, filed Oct. 15, 2010, now abandoned, and pending U.S. patent application Ser. No. 13/831,239, filed Mar. 14, 2013, now U.S. Pat. No. 9,308,343, issued Apr. 12, 2016. The entire specifications of all four applications are incorporated by reference herein.

FIELD OF THE INVENTION

The present invention relates, in general, to equipment used in the treatment of sleep apnea and other respiratory ailments and, more particularly, the instant invention relates to an improved apparatus to deliver a fluid pressure to both the nasal and oral airway passages of a patient in order maintain the patient's airway open while sleeping and deliver oxygen to such patient.

BACKGROUND OF THE INVENTION

As is well known in the medical field, sleep apnea is a disorder that affects more than 12 million people in the United States alone. It takes its name from the Greek word apnea, which means "without breath." People with sleep apnea literally stop breathing repeatedly during their sleep, often for a minute or longer, and as many as hundreds of times during a single night.

Sleep apnea is known to be caused by either complete obstruction of the airway (obstructive apnea) or partial obstruction (obstructive hypopnea), both of which can cause the person suffering from such sleep apnea to wake up, temporarily, in order to breathe. There are three types of sleep apnea—obstructive, central, and mixed. Of these, obstructive sleep apnea (OSA) is the most common. OSA occurs in approximately 2 percent of women and 4 percent of men over the age of 35.

The exact cause of OSA remains unclear. The site of obstruction in most patients is the soft palate, extending to the region at the base of the tongue. There are no rigid structures, such as cartilage or bone, in this area to hold the airway open. During the day, muscles in the region keep the passage wide open. But as a person with OSA falls asleep, these muscles relax to a point where the airway collapses and breathing becomes impossible. When breathing stops, the sleeper partially awakens, involuntarily tenses the muscles in the region to open the airway in order to breathe, and falls back asleep. The arousal from sleep usually lasts only a few seconds, but these brief arousals disrupt continuous sleep and prevent the person from reaching the deep stages of slumber, such as rapid eye movement (REM) sleep, which the body needs in order to rest and replenish its strength. Even though normal breathing is restored when the person awakens briefly, the cycle is repeated throughout the night. Typically, the frequency of waking episodes is somewhere between 10 and 60, although a person with severe OSA may have more than 100 waking episodes in a single night.

Positive airway pressure has been demonstrated to be a very effective treatment for obstructive sleep apnea. It has three forms: continuous positive airway pressure (CPAP), autotitration, and bi-level positive airway pressure (BIPAP). While positive airway pressure is usually easier to tolerate at lower pressures, every patient requires a different pressure. In order to determine each individual patient's optimum airway pressure, it is necessary to titrate the pressure to each individual patient during a polysomnogram. A polysomnogram will show not only when the respiratory events have ceased, but also when the arousals from the respiratory events occur.

CPAP, the most common of the three therapy modes, is usually administered at bedtime through a facial mask held in place by straps around the patient's head. The mask is connected by a tube to a small air compressor about the size of a shoe box. The CPAP machine sends air under pressure through the tube into the mask, where, assuming a good seal with the patient's face, it applies a positive air pressure to the upper airways. This positive air pressure essentially "splints" the upper airway open and keeps it from collapsing.

Approximately 55 percent of patients who use CPAP do so on a nightly basis for more than four hours. The advantages of CPAP are that it is very safe and completely reversible. Generally, the treatment is well tolerated; however, it suffers from the disadvantage that it requires active participation every night; that is, the patient must put it on for it to work. If the mask is ill-fitting or causes unwanted side effects, compliance will not be maintained.

CPAP Masks on the market today fall into one of three design categories. They are either nasal masks, full face masks (i.e., those which cover the mouth and nose) or nasal pillows. The vast majority of CPAP masks that are currently on the market are comprised of a rigid plastic frame buffered by an elastomeric, rubbery "cushion" that makes the actual contact with the patient's face. These masks are sealed to the patient's face by tightening straps that hold the mask to the patient's head to increase mechanical pressure against and into the skin of the face. The skin and tissue of the patient's face is compressed by the mask, which forms a "gasket" that creates a seal and keeps the air pressure inside the mask elevated. Unfortunately, aside from being uncomfortable, a disadvantage to this approach is that the mechanical pressure applied to the patient's skin often exceeds the perfusion pressure in the tissue under the skin. Consequently blood flow to the tissue is diminished or cut off entirely. This leads to pain and can ultimately cause pressure sores on the patient's face. Additionally, it has been discovered that some of the masks, which use a silicone or a polyurethane gel to touch the face, have caused allergic reactions in some users.

These problems were largely overcome by the soft cloth mask disclosed in U.S. patent application Ser. No. 12/070,463, (the "'463 application"). The '463 application disclosed a nasal CPAP mask that was entirely comprised of a non-rigid, compliant material that had no fixed shaped unless breathable gas at positive pressure was flowing into it. While the nasal mask of the '463 application remedied many of the drawbacks with then-existing masks, many sleep apnea sufferers are either unable to use a nasal only mask or simply prefer a full face mask. Many people with sleep apnea sleep with their mouths open, which is problematic with a nasal respiratory mask because the therapy is bypassed if the user breathes through their mouth instead of the mask.

Another problem with full face masks is the difficulty of putting the mask on and taking it off. Further, since there is even more variability in facial structure when the mouth and jaw are involved than with nasal masks, obtaining a good seal remains a significant problem with full face masks.

Still another problem with existing full face masks is that in order to keep the mask in place and sealed on the user's face, significant pressure must be placed on the chin of the user. This added pressure is not only uncomfortable, it can be counterproductive to sleep apnea therapy because it has the potential to push the jaw back, which can exacerbate the very problem that the therapy is was prescribed to solve.

Additionally, full face masks cover the user's mouth by their very nature, which makes it difficult for a person receiving therapy to be able to talk while still receiving therapy. The plastic mask makes this even more difficult in that the patient's voice is muffled so that the patient cannot verbally communicate to anyone while wearing the mask.

These problems with prior art masks collude to ultimately make it less likely that the patient will continue the therapy. The present invention therefore seeks to overcome or at least ameliorate these problems associated with the prior art type devices.

SUMMARY OF THE INVENTION

It is, therefore, one of the primary objects of the present invention to provide a full face respiratory mask for delivering a positive fluid pressure to a patient's nasal and oral air passageways which is easier to put on and remove than existing masks.

Another object of the present invention is to provide a full face apparatus for delivering a positive fluid pressure to a patient's air passageways that is more comfortable and doesn't place as much pressure on the chin or jaw area as other current full face masks.

Yet another object of the present invention is to provide a full face mask for delivering a positive fluid pressure to a patient's air passageways having substantially improved air sealing capability and better fit.

An additional object of the present invention is to provide a full face mask for delivering a positive fluid pressure to a patient's air passageways wherein substantially all portions of such apparatus that touch the patient's face are made of a soft and flexible material that is moisture-vapor breathable.

Another object is to provide a full face mask that enables the wearer to carry on a conversation while therapy is being administered.

A still further object of the present invention is to provide a full face respiratory mask that is substantially capable of conforming to a patient's facial features without using excess pressure to force the mask to fit on the patient's face.

Yet another object of the present invention is to provide a full face respiratory mask having no rigid parts to press against the patient's skin while the patient sleeps.

In addition to the various objects and advantages of the present invention which have been described above, various other objects and advantages of the invention will become more readily apparent to those persons skilled in the relevant art from the following more detailed description of the invention, particularly, when such description is taken in conjunction with the attached drawing figures and with the appended claims.

DETAILED DESCRIPTION OF THE INVENTION

Prior to proceeding to the more detailed description of the instant invention it should be noted that identical components having identical functions have been designated with identical reference numerals throughout the several views illustrated in the drawings for the sake of clarity.

As used in the present specification and claims, the term "cloth body" means that portion of the mask that inflates as a result of the delivery of air from a pump through a tube with a swivel connector, including that portion that actually makes contact with the patient's nose and face when the CPAP mask is being used as intended.

As used in the present specification and claims, the term "compliant" means a material having very little rigidity such that it is easily bendable.

The term "inflatable" as used herein, means a material or a structure having two configurations: an uninflated configuration and an inflated configuration that is different from the uninflated configuration.

As used herein, the term "cloth" is meant to include natural and synthetic fiber cloth, treated cloth, laminates having a cloth base and cloth which is permeable or impermeable to air.

The Mask

Figure 1:
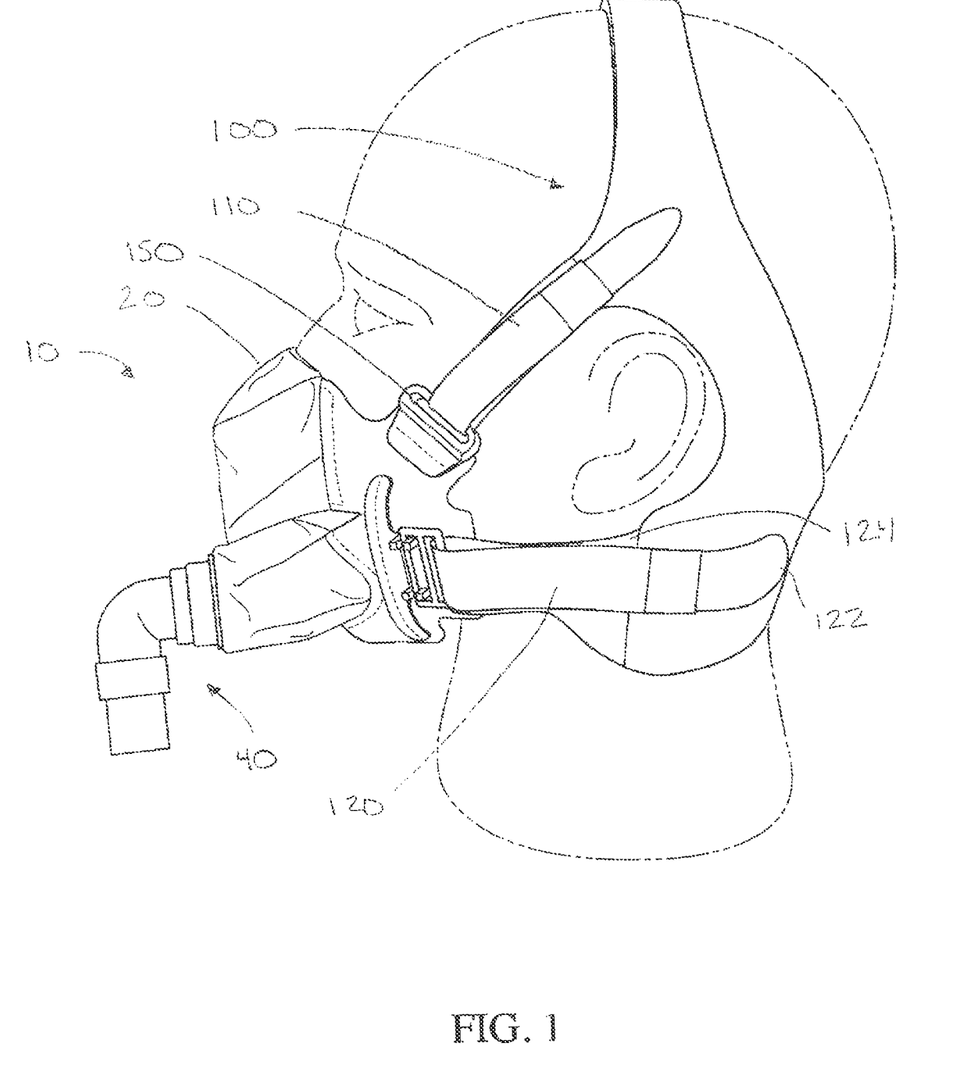
FIG. 1 is a side view of a full face mask of the present invention wherein the mask is inflated and being used by a patient.
Figure 2:
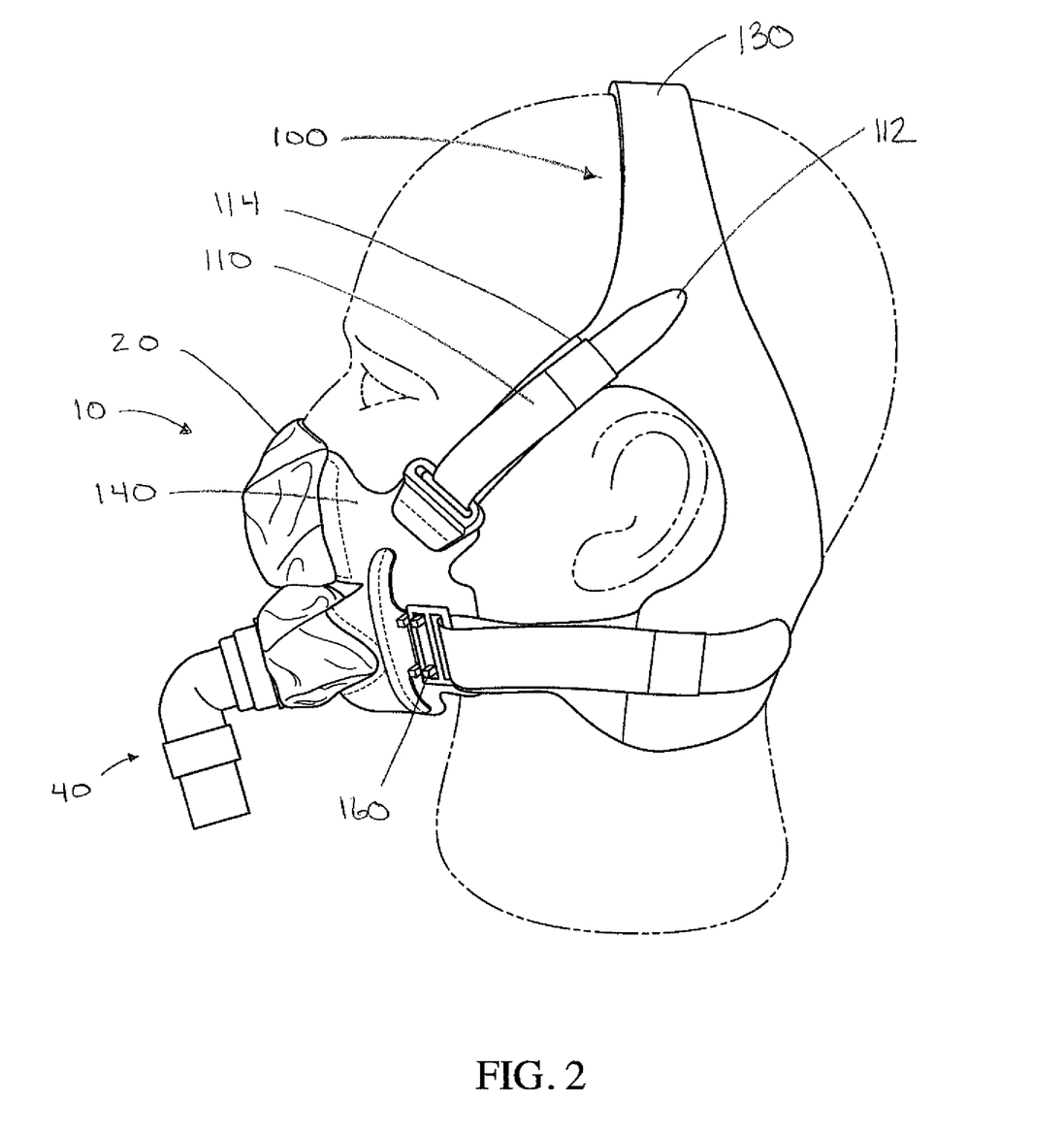
FIG. 2 is a side view of a presently preferred embodiment of the invention wherein the mask is uninflated and is not in use.

Now referring more particularly to FIGS. 1 and 2, the presently preferred embodiment of an apparatus, generally designated 10, for communicating a positive fluid pressure to a patient's nasal and oral air passageways is illustrated. In FIG. 1, the mask 20 is illustrated in an inflated configuration and in FIG. 2, the mask 20 is shown in an uninflated configuration. When in the uninflated configuration, the mask is not sealed to the face, but when air at a pressure is supplied to the mask 20 through an air delivery arrangement 40, equal pressure is applied to all areas inside the mask 20 and causes it to be pressed against the user's face.

In a preferred embodiment, the majority of the mask 20 is comprised of an inelastic yet flexible composite material that is relatively impermeable to gas and is soft to touch. Preferably, this composite material is moisture-vapor breathable and comprised of a polyester cloth having a flexible coating such as a polyester or polyurethane film disposed on an inner surface.

Figure 3A:
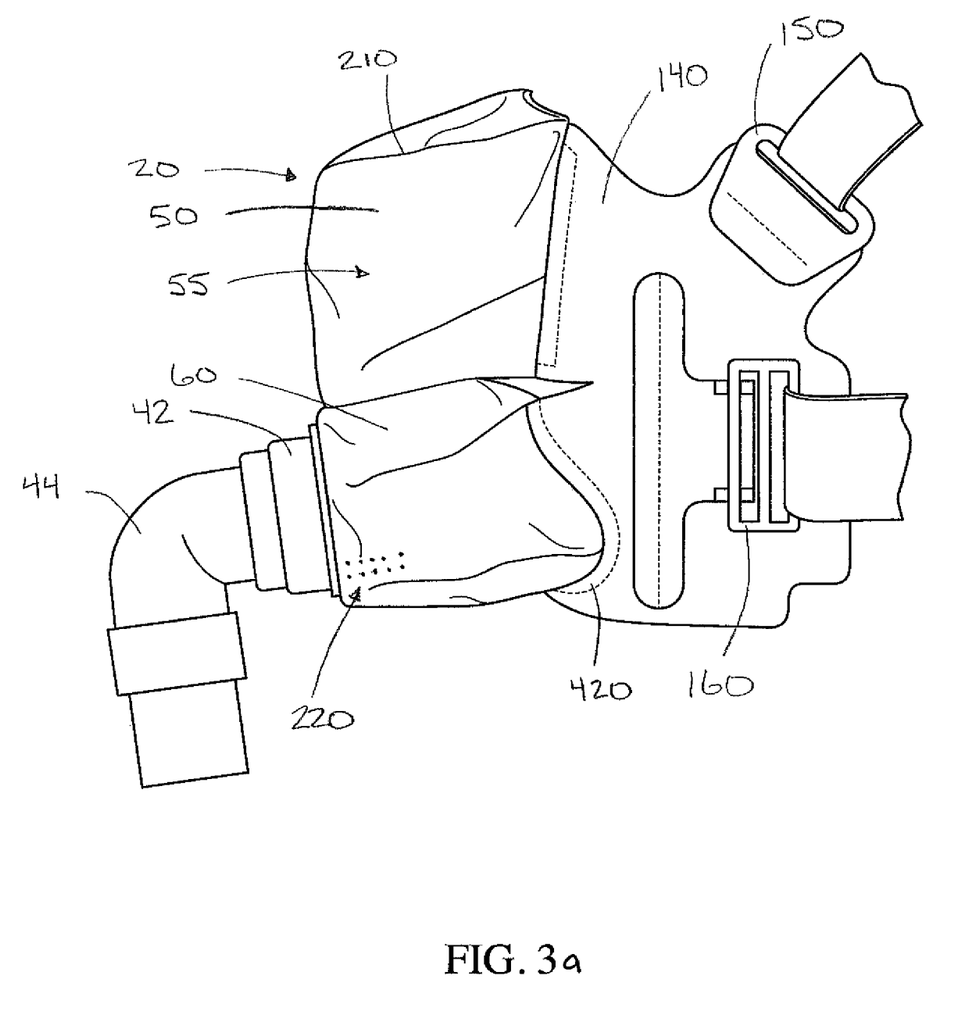
FIG. 3a is an elevated view of an embodiment of the mask of the present invention.
Figure 3B:
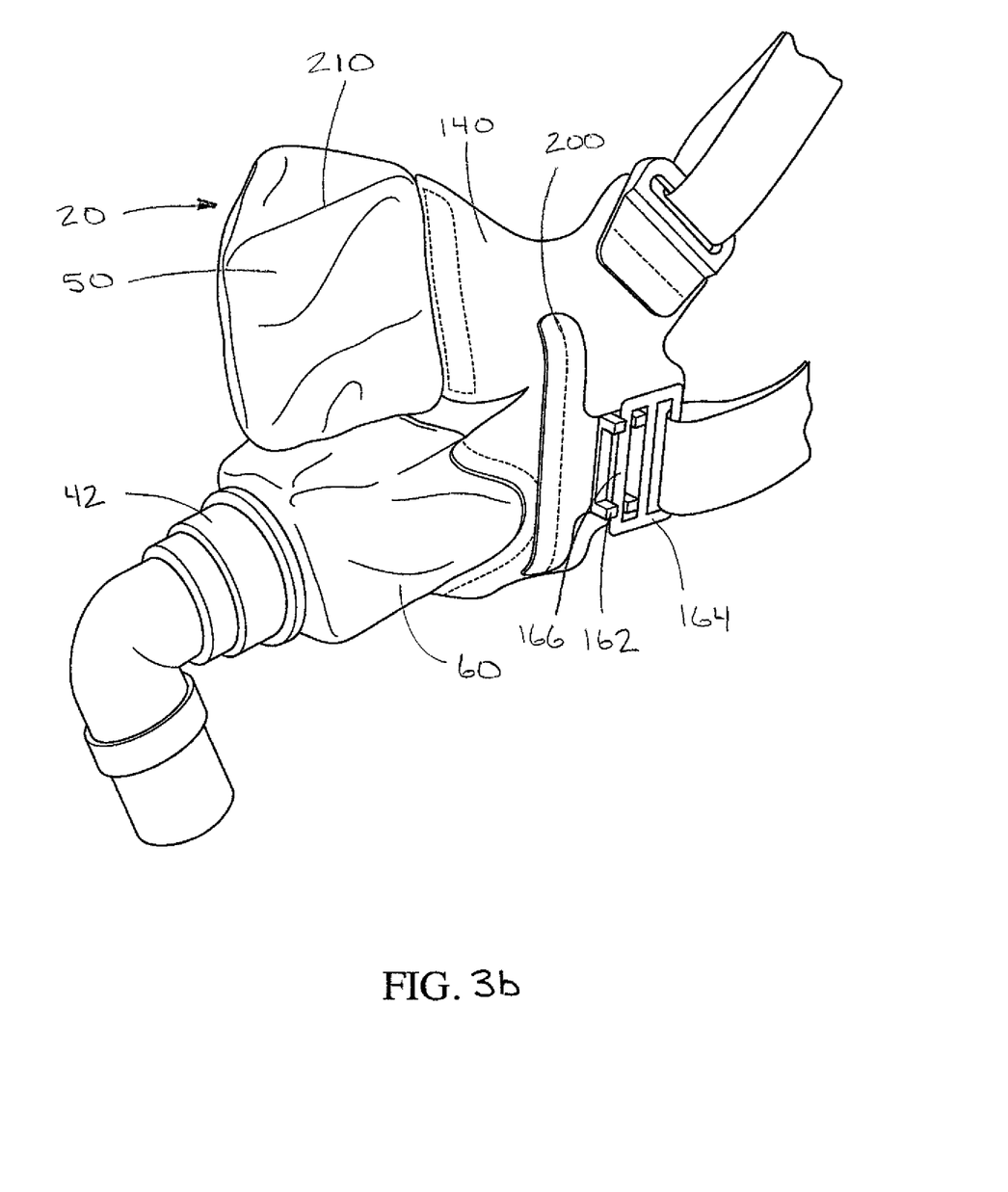
FIG. 3b is a perspective view of an embodiment of the mask of the present invention.
Figure 3C:
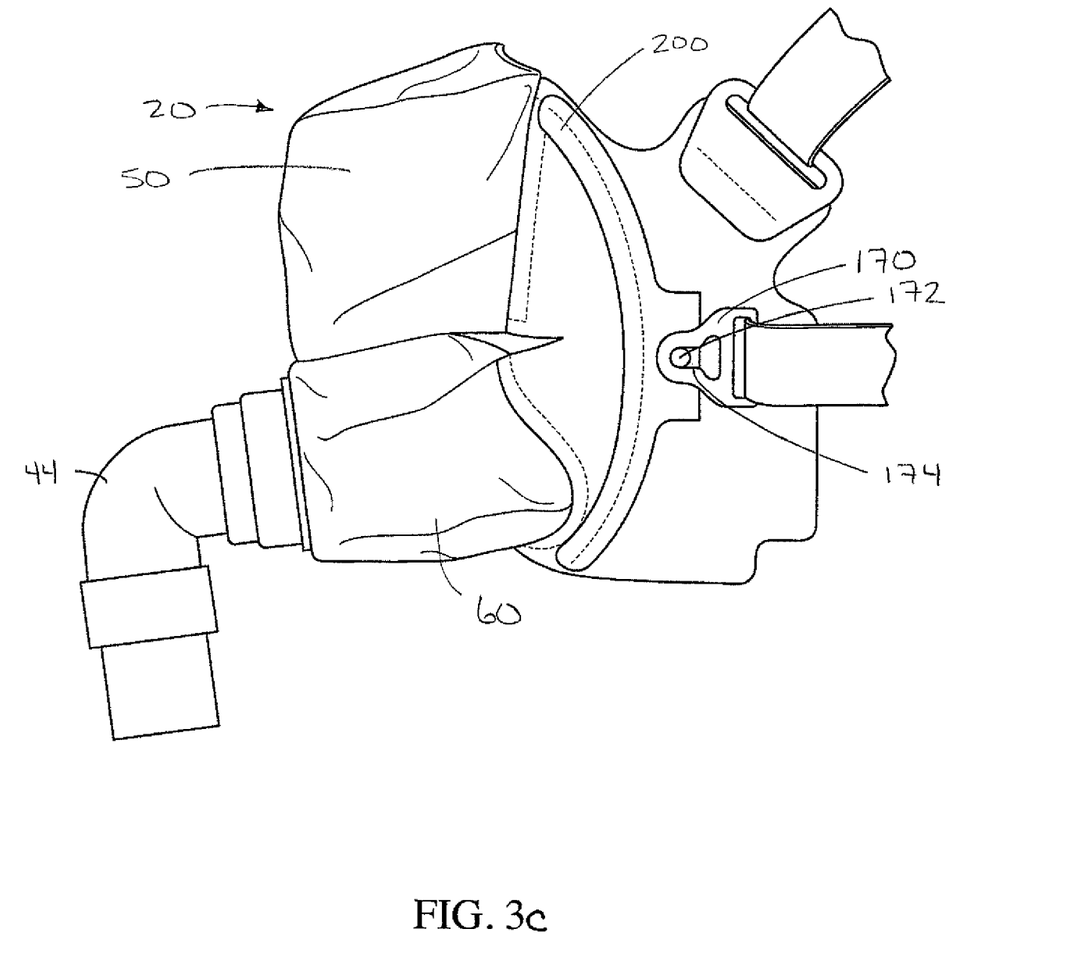
FIG. 3c is an elevated view of an alternative embodiment of the mask of the present invention.
Figure 4:
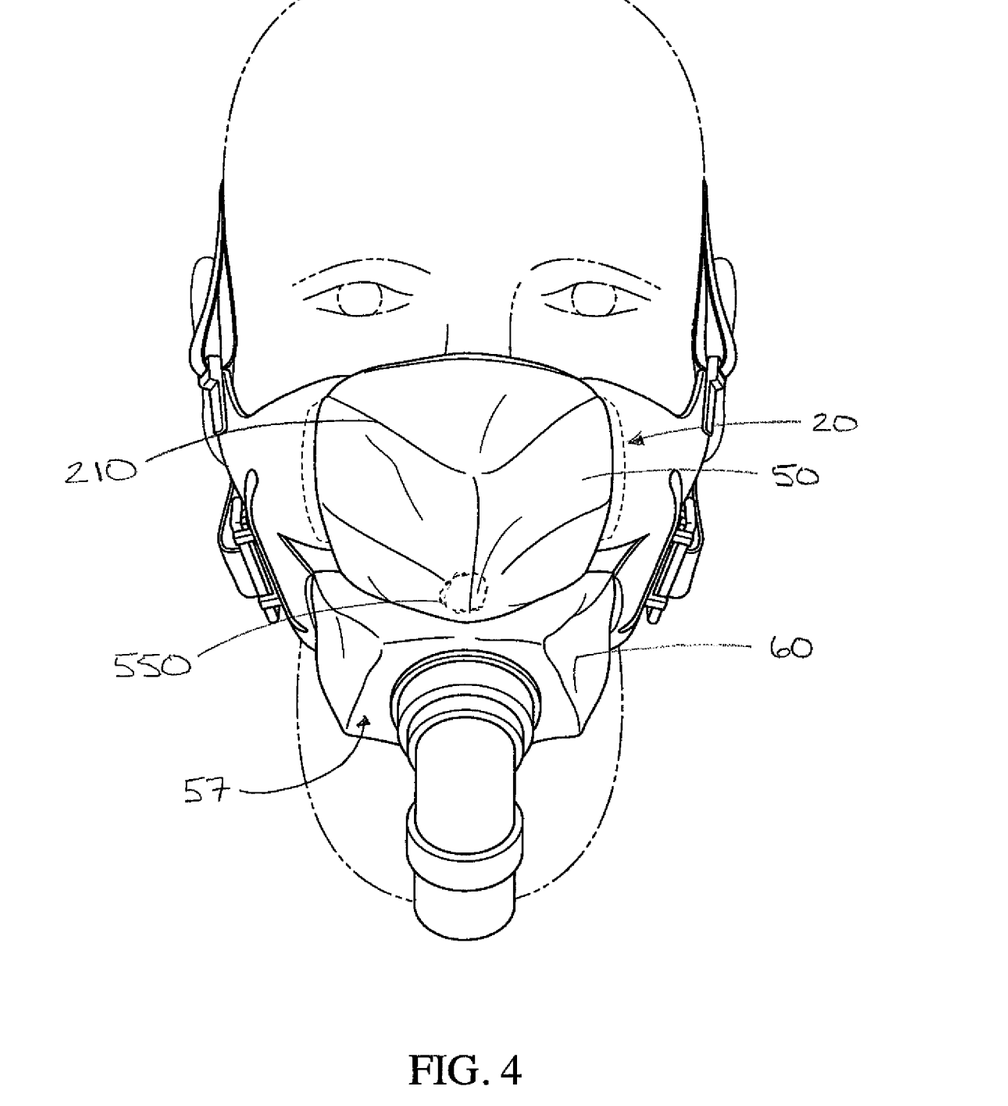
FIG. 4 is a front view of an embodiment of the present invention wherein the mask is being used by a patient.
Figure 5:
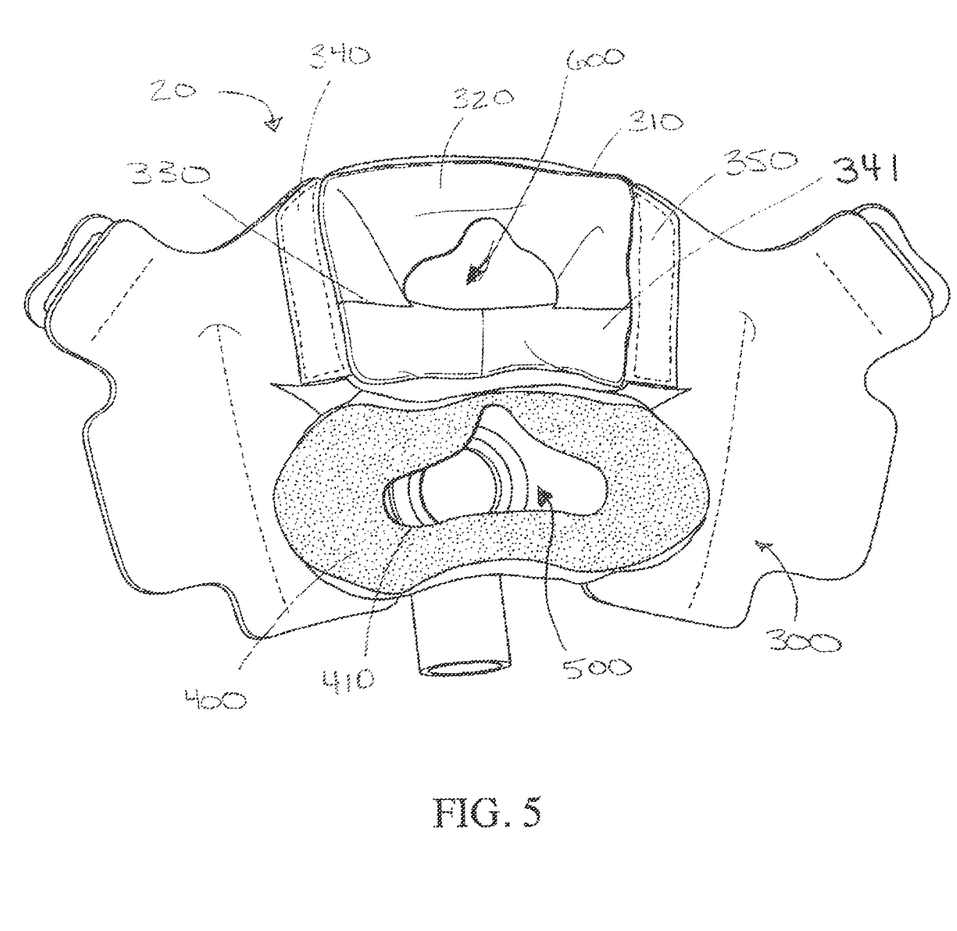
FIG. 5 is a perspective view of the inner side of the mask of the present invention.
Figure 6:
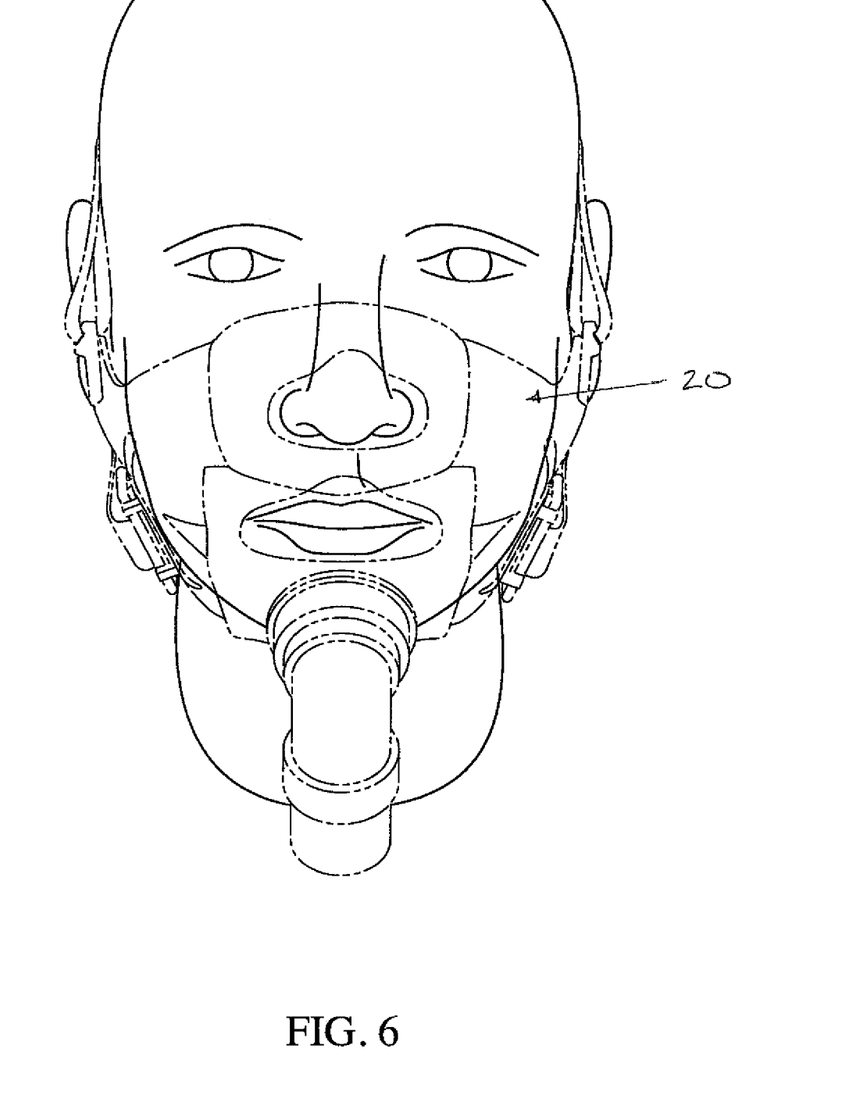
FIG. 6 is a front view of the mask of the present invention wherein the apertures for the user's nose and mouth are demonstrated when the mask is in place on the user.

Referring to FIGS. 3a-3c and 4, the outer side 55 of the mask 20 is again shown. It can be seen that the mask 20 is constructed with two fluidly connected portions: a nasal portion 50 and an oral portion 60 such that, in use, air at a pressure is delivered via the air delivery arrangement 40 into the oral portion 60 after which, it passes into the nasal portion 50, and the pressure substantially equilibrates between the two portions so that both portions are inflated and a specific air pressure is delivered to the user's air passageways through apertures in the inner surfaces of both the oral portion and the nasal portion. In an embodiment, the two portions 50, 60 are connected by an internal shared aperture 550 within the mask 20 at the bottom of the nasal portion 50 and the top of the oral portion 60. FIG. 5 shows an inner surface 300 of both the oral portion 60 and the nasal portion 50. The oral portion has an oral aperture 500 and the nasal portion has a nasal aperture 600. The oral aperture and the nasal aperture are fluidly connected via the internal shared aperture that is shared by the upper oral portion and the lower nasal portion as would be clear to one of skill in the art and this internal shared aperture 550 is illustrated in FIG. 4.

The oral portion 60 and the nasal portion 50 both have lateral edges that are sewn or otherwise disposed on a cloth transition portion 140 of the mask. In contrast with the material used in the oral portion 60 and nasal portion 50, these transition portions are comprised of a polyurethane foam that, in embodiments, is coated with a nylon and lycra combination to give them some stretchiness. The transition portions 140 bilaterally disposed on both sides of the oral and nasal portions of the mask and are discussed in greater detail below.

The Nasal Interface

With reference to FIG. 5, an inner surface 300 of the mask 20 is illustrated. This is the portion of the mask that touches the user's face during therapy. Generally, a nasal interface 310 situated vertically adjacent to the nasal portion 50 of the mask is designed to comfortably make contact with the nose and face of a user and is manufactured using an elastic moisture-vapor breathable material that is sewn or otherwise disposed onto the mask 20 from the inner surface 300. As used herein, the term "moisture-vapor breathable" refers to a fabric or other material that allows water vapor to pass through it from one side to the other. Moisture-vapor breathable materials are used because it has been shown that very small amounts of moisture within or under a mask can create the sensation of discomfort in a patient. Often, a mere 3% to 5% of increase in humidity is enough to create discomfort. If liquid water from sweating or exhalation cannot be dissipated quickly, as is the case with prior art nasal masks that use a silicone or polyurethane gel that contacts the skin, the humidity of the air in the space in between the skin and the cloth body rises. This increased humidity prevents rapid evaporation of liquid water on the skin and creates an increased sensation of heat, which, ironically, is what triggered the sweating in the first place. Consequently, the body responds with increased sweating to dissipate the excess thermal energy, which feeds into an unfortunate cycle of increased humidity and discomfort for the patient. The advantage of using a moisture-vapor breathable material, then, is that moisture and heat are wicked away from the skin as the cloth body is worn, which increases comfort, improves compliance, reduces heat, and reduces the moisture build-up at the cloth body contact area for the patient.

In a preferred embodiment, the elastic moisture-vapor breathable material used for the nasal interface 310 is a nylon and elastane combination (also referred to as Lycra®) with a polyurethane backing, which all together, is comprised of preferably seventy-two (72%) percent nylon (where the term nylon includes both the stretchy elastane and the nylon) and twenty-eight (28%) percent polyurethane. Further describing this preferred material, it weighs 138 grams per square meter, has waterproofness of 10,000 millimeters of water, and has tear strength of 18.4 Newtons× 11.6 Newtons. Additionally, the moisture-vapor breathable material of the preferred embodiment has a moisture permeability of a range of approximately fifteen thousand to thirty-eight thousand (38,000) grams per meter squared per 24 hours using the Inverted Cup test JIS-L 1099 B-1.

In an alternative embodiment, the material used for the nasal interface 310 comprises fifty-six (56%) percent nylon, twenty-two (22%) percent elastane and twenty-two (22%) percent polyurethane. Further describing this material, it weighs 90 grams per square meter, has a moisture-vapor breathability transmission rate of 8,000 grams per meter squared per 24 hours using the ISO 15496 measurement method, a water proofness of greater than 10,000 millimeters of water using ISO 811 and has a breaking strength of 200 Newtons measured using the ISO 13934/1 test method. Other combinations of materials that accomplish the same task, however, will be apparent to those of skill in the art.

With continued reference to FIG. 5, the nasal interface 310 comprises at least a nose cradling portion 320 and an upper lip portion 330, each of the portions having a first vertical edge 340 and a second vertical edge 350. The linear amount of material, measured laterally, from the first vertical edge 340 to the second vertical edge 350 is greater for the nose cradling portion 320 than for the upper lip portion 330 in order to comfortably and fittingly accommodate the patient's nose when the mask 20 is worn. The shape that is created by the combination of the nose cradling portion 320 and the upper lip portion 330, in conjunction with the elastic and stretchy quality of the material will cause it to naturally conform to the patient's nose as opposed to being stretched over the nose in an overly taut and uncomfortable manner. Additionally, the upper lip portion 330 has at least one wrapped section 341 that provides a soft contact point with the user's upper lip and is loosely and slidingly sleeved around an inner section (under the shown sleeved section), which provides a mechanism for increased width of the cloth body without sacrificing comfort. When the upper lip portion is stretched, such as with users with wider faces, the stretchy inner section becomes firmer than other portions of the mask and the wrapped section protects the user's upper lip against this firmness for additional comfort.

When the CPAP machine is turned on and the mask placed on a user, the air pressure will build in the mask and inflate the oral and nasal portions 60, 50 and, in conjunction with the headgear 100, cause the nasal interface 310 to gently and evenly push against the patient's skin to create the necessary seal. In this manner, it can be seen that the addition or removal of air pressure causes the oral and nasal portions 60, 50 to move between two different configurations: an uninflated configuration and an inflated configuration.

The Oral Interface

With further reference to FIG. 5, an oral interface 400 is disposed on the inner surface 300 and is generally oval-shaped with a smaller generally oval-shaped aperture 410 formed therein. This interface 400 is an additional layer of material generally disposed on the inner surface 300 of the mask 20 below the nasal interface 320 and disposed on the inner surface 300 of the oral portion 60 of the mask. In an embodiment, the oral interface 400 is manufactured with a material comprising elastane, polyurethane, nylon and polyester. In another embodiment, the composition is 7% elastane, 22% polyurethane, 32% nylon, and 39% polyester. Further describing this material, it weighs 345 grams per square meter, has a moisture-vapor breathability transmission rate of 5000 grams per meter squared per 24 hours using the ISO 15496 measurement method, a water proofness of greater than 10,000 millimeters of water using the ISO 811 testing method and has a breaking strength of 900 newtons warp and 450 newtons weft using the ISO 13934/1 testing method.

In order to push the oral interface 400 closer to the face, an inner edge 420 of the cloth transition portion 140 of the mask (as seen on FIG. 3*a*) is sewn from the outside of the mask onto the oral portion 60, which then overlaps the oral interface 400 slightly so that a small amount of additional force is applied to the oral interface 400 when the mask 20 is in place to assist in maintaining the desired seal during therapy.

Air Delivery Arrangement

FIGS. 3*a*-3*c* and FIG. 4 illustrate an air delivery arrangement 40 that enables air to be sealingly delivered to the mask 20 through a circular aperture on the front surface 57 of the oral portion 60 of the mask. In an embodiment, a connector ring 42 is matingly and sealingly connected to an internal connector and gasket on the inside of the mask, such as by a mated threading system or similar. Also, the connector ring 42 is rotatingly connected to an elbow 44 to permit 360 degree axial rotation of the elbow 44 about the clamp axis. Preferably, the elbow 44 contains an anti-asphyxia mechanism as is well-known in the art.

In an embodiment, the internal connector is tubular in form with an external flange on one end and is threaded on its exterior surface to enable a tight connection with the connector ring 42, which can be matingly threaded on its interior surface. Further, there is preferably a washer that is inserted between the internal connector and the connector ring 42 to protect the material of the oral portion 60 when the connector ring 42 is screwed into place, and to form a more perfect airtight seal. As will be apparent to those of skill in the art, other means of connecting the connector ring 42 with internal connector, such as a snap fit arrangement, can be used.

The Headgear and the Transition Portion of the Mask

With continued reference to FIGS. 1-3*c*, the mask 20 is held in place with headgear 100 that includes an upper strap 110 and a lower strap 120 on both sides and a head portion 130 that wraps around the back of the user's head. The headgear is manufactured with a polyurethane foam that, in embodiments is optionally coated with a nylon and lycra combination, and works in conjunction with the air pressure to seal the mask to the user's face. The upper strap 110, which is attached to the transition portion 140 on both sides of the mask 20 at an angle of approximately 45 degrees to horizontal, is connected to the mask via loop connectors 150. In an embodiment, the lower strap 120 is slidingly connected near a first end to the transition portion 140 of both sides of the mask 20 with snap clips 160 to facilitate placement and removal of the mask 20 from the user's head. The lower strap 120 further comprises a fastener, such as a hook and loop system, at a first end 122 that is slid through the snap clip 160 and adjustably looped back to connect to itself in a manner well-known in the art. A second end 124 of the lower strap 120 is disposed on the head portion 130 on both sides of the headgear 100. In like fashion, the upper straps 110 are connected to the transition portions 140 by sliding a first end 112 through the loop connector 150 and adjustably attaching them to themselves via a fastener such as a hook and loop system. The second end 114 of the upper straps 110 is disposed on the head portion 130 on both sides of the headgear 100.

With reference to FIG. 3*b*, the snap clips 160 have a base 162 sized to snappingly accept a connector 164 when pressure is applied against the base 162 with a bar portion 166 of the connector 164. FIG. 3*c* illustrates a removable clip 170 of another embodiment wherein a protrusion 172 of having a certain diameter is caught within a clip having a slot 174 with a smaller diameter than the protrusion 172.

FIGS. 3*b* and 3*c* also serve to highlight two different embodiments of a sealing assistance member 200 that serves to keep the transition portion 140 of the mask in close conformance with the user's face. In a first embodiment, the sealing assistance member 200 is plastic and is sewn into the transition portion 140 of the mask. The member 200 is further curved inward slightly at the first and second ends to assist with creating a seal on the user's face. The second embodiment shown in FIG. 3*c* shows a member 200' that is also sewn into the transition portion 140 and curvably extends the entire height of the transition portion 140 to add structure to the mask and facilitate a better seal with the user's face. Preferably, the sealing assistance member 200, 200' is unitary with the snap clip 160.

The Exhalation System

A CPAP mask must have an exhalation system in order to facilitate the removal of carbon dioxide exhaled by the user. The oral portion 60 and nasal portion 50 of the mask 20 of the present invention have seams 210 where pieces of fabric have been stitched together with thread and these seams 210 function as part of the exhalation system in order to obtain an appropriate leak rate while still maintaining a minimal noise level so that the user's bed partner is not disturbed. Since each stitch is created by making a tiny hole in the fabric for the stitch and pulling the two separate pieces of fabric tightly together, the leak rate of a mask 20 can be modified by adjusting the length of fabric sewn together along with the number of stitches per inch.

In a preferred embodiment, then, it has been determined that the optimal leak rate is achieved through the use of between 6 and 30 stitches per inch in conjunction with of a plurality of exhalation apertures 220. It has been discovered that the larger the mask, the longer the seams are and the fewer exhalation apertures 220 are needed. So, in an embodiment for a large mask, a number of apertures in the range of 90 are necessary to provide the optimal exhalation rate for a given therapeutic pressure whereas a smaller mask requires more, such as a number in the range of 110 apertures, for the same therapeutic pressure and exhalation rate. In embodiments, the number of exhalation apertures 220 can range from ten (10) to one hundred fifty (150) with each individual aperture being in a range of 0.004 and 0.006 inches in diameter. Further, while the exhalation apertures 220 illustrated in FIG. 3*a* are on the side of the cloth body, it is preferable that they be placed on the bottom to minimize the chance of any air being blown on a sleeping partner.

If not otherwise stated herein, it is to be assumed that all patents, patent applications, patent publications and other publications (including web-based publications) mentioned and cited herein are hereby fully incorporated by reference herein as if set forth in their entirety herein.

While in accordance with the patent statutes the presently preferred and various alternative embodiments of the instant invention have been described in detail above, it should be understood that various other modifications and alternatives can be envisioned by those persons skilled in the art without departing from either the spirit of the invention or the scope of the appended claims.

We claim:

1. A respiratory mask for noninvasively supplying air from an air hose to a user's nasal passages at a therapeutic pressure, comprising:

a cloth body comprising a moisture-vapor breathable cloth material, having a first inflated configuration where the presence of the supplied air cooperates with the material to create a chamber maintaining a fixed shape and a second uninflated configuration where the fixed shape is not maintained due to the absence of supplied air, the cloth body having a proximal surface with a nasal interface that forms a seal around the user's nasal passages and a distal surface having a substantially circular aperture formed therein;

an air delivery arrangement comprising an elbow and an internal connector; the elbow having a first end and a second end, the first end sealingly disposed on the air hose and the second end having a connector ring that sealingly mates with the internal connector, whereby the internal connector and connector ring cooperatively clamp the cloth body material around the circumference of the aperture and sealingly connect the air delivery arrangement to the cloth material of the cloth body;

whereby air at the therapeutic pressure is supplied through the air delivery arrangement to the mask and inflates the cloth body, causing it to assume and maintain the first inflated configuration and to resist deformation when the air at the therapeutic pressure is applied; and an exhalation system.

2. The respiratory mask of claim 1, wherein the nasal interface further has an aperture formed therein for delivering air at the therapeutic pressure to the user's nasal passages.

3. The respiratory mask of claim 1, wherein the second end of the elbow extends through the substantially circular aperture in the distal surface of the cloth body and into the chamber and enables the connector ring and the internal connector to clamp the cloth body material.

4. The respiratory mask of claim 1, wherein the internal connector extends through the substantially circular aperture in the distal surface of the cloth body and out of the chamber and engages with the connector ring to cooperatively clamp the cloth body material.

5. The respiratory mask of claim 1, wherein the cloth material is comprised of a polyester cloth having a flexible coating comprising one of a polyester film or a polyurethane film.

6. The respiratory mask of claim 1, wherein the cloth material is substantially comprised of polyester, polyurethane, elastane and nylon.

7. The respiratory mask of claim 1, wherein the exhalation system comprises a plurality of apertures.

8. The respiratory mask of claim 7, wherein the exhalation system further comprises seam apertures.

9. The respiratory mask of claim 1, further comprising headgear and bilaterally disposed transition portions that connect the mask to the headgear.

10. The respiratory mask of claim 9, wherein the transition portions comprise snap clips for easy removal and placement.

11. A method of hermetically sealing an air delivery arrangement having an elbow, a connector ring disposed on the elbow, and an internal connector, to a respiratory mask having a cloth body, the method comprising:
    forming a substantially circular aperture having a first diameter in a distal surface of the cloth body;
    extending the air delivery arrangement having a second diameter through the substantially circular aperture by extending the elbow through the substantially circular aperture; and
    capturing the cloth body at the circumference of the substantially circular aperture between the connector ring and the internal connector.

12. The method of claim 11, wherein the connector ring and the elbow are threaded.

13. The method of claim 12, wherein the capturing step further comprises threadingly connecting the elbow and the internal connector until the internal connector abuts the connector ring.

14. The method of claim 11, wherein the first diameter is substantially the same as the second diameter.

15. The method of claim 11, wherein the capturing step further comprises inserting a gasket between the internal connector and the cloth body.

16. A method of hermetically sealing an air delivery arrangement having a connector ring and an internal connector, to a respiratory mask having a cloth body, the method comprising:
    forming a substantially circular aperture having a first diameter in a distal surface of the cloth body;
    extending the air delivery arrangement having a second diameter through the substantially circular aperture;
    inserting a gasket between the internal connector and the cloth body; and
    capturing the cloth body at the circumference of the substantially circular aperture between the connector ring and the internal connector.

17. The method of claim 16, wherein the air delivery arrangement further comprises an elbow with the connector ring disposed thereon and the step of extending the air delivery arrangement through the substantially circular aperture further comprises extending the elbow through the substantially circular aperture.

18. The method of claim 17, wherein the connector ring and the elbow are threaded and the capturing step further comprises threadingly connecting the elbow and the internal connector until the internal connector abuts the connector ring.

19. The method of claim 16, wherein the first diameter is substantially the same as the second diameter.

\* \* \* \* \*